(12) United States Patent
Matsuda et al.

(10) Patent No.: US 8,748,155 B2
(45) Date of Patent: Jun. 10, 2014

(54) PROTEIN EXHIBITING ACTIVITY OF PYRETHRIN BIOSYNTHETIC ENZYME, GENE ENCODING THE PROTEIN, AND VECTOR BEARING THE GENE

(71) Applicants: An Educational Foundation Kinki University, Higashiosaka (JP); Dainihon Jochugiku Co., Ltd., Osaka (JP)

(72) Inventors: Kazuhiko Matsuda, Nara (JP); Yukio Kikuta, Toyonaka (JP)

(73) Assignees: An Educational Foundation Kinki University, Osaka (JP); Dainihon Jochugiku Co., Ltd., Osaka (JP)

( * ) Notice: Subject to any disclaimer, the term of this patent is extended or adjusted under 35 U.S.C. 154(b) by 0 days.

(21) Appl. No.: 13/720,574

(22) Filed: Dec. 19, 2012

(65) Prior Publication Data
US 2013/0109076 A1 May 2, 2013

Related U.S. Application Data

(63) Continuation-in-part of application No. 13/137,327, filed on Aug. 5, 2011, which is a continuation-in-part of application No. 12/457,193, filed on Jun. 3, 2009, now Pat. No. 8,129,180.

(30) Foreign Application Priority Data

Aug. 13, 2008 (JP) ................................. 2008-208295

(51) Int. Cl.
| | |
|---|---|
| *C12N 1/21* | (2006.01) |
| *C12N 9/10* | (2006.01) |
| *C12N 15/11* | (2006.01) |
| *C12N 15/54* | (2006.01) |
| *C12N 15/62* | (2006.01) |
| *C12N 15/63* | (2006.01) |

(52) U.S. Cl.
USPC ............... 435/252.3; 435/193; 435/320.1; 536/23.1; 536/23.2; 536/23.4; 536/23.6; 560/350; 560/370

(58) Field of Classification Search
None
See application file for complete search history.

(56) References Cited

U.S. PATENT DOCUMENTS

| | | | | |
|---|---|---|---|---|
| 8,124,074 B2 * | 2/2012 | Foster et al. | ............... | 424/94.63 |
| 2010/0062510 A1 * | 3/2010 | Matsuda et al. | ........... | 435/320.1 |

FOREIGN PATENT DOCUMENTS

| | | |
|---|---|---|
| EP | 0 124 049 A2 | 11/1984 |
| JP | A-9-504684 | 5/1997 |
| WO | WO 95/00634 A1 | 1/1995 |

OTHER PUBLICATIONS

Kikuta et al., Identification and characterization of GDSL lipase-like protein that catalyzes the ester-forming reaction for pyrethrin biosynthesis in *Tanacetum cinerariifolium*, Plant J., 2012, 71, 183-93.*
GenBank Accession No. JN418894.1, Feb. 2012, www.ncbi.nlm.nih.gov.*
Cloning Vector pMAL-c4E, complete sequence, Oct. 22, 2007, www.neb.com/tools-and-resources/interactive-tools/dna-sequences-and-maps-tool.*
Purification System, New England BioLabs, 2006.*
GenBank Accession No. JN418990.1, Feb. 2012, www.ncbi.nlm.nih.gov.*
R. Kalscheuer and A. Steinbuchel, A Novel Bifunctional Wax Ester Synthase/Acyl-CoA: Diacylglycerol Acyltransferase Mediates Wax Ester and Triacylglycerol Biosynthesis in Acinetobacter calcoaceticus ADP1. J. Biol. Chem. 278:8075-8082 (2003).
J. Luo et al., Convergent evolution in the BAHD family of acyl transferases: identification and characterization of anthocyanin acyl transferases from *Arabidopsis thaliana*. Plant J. 50:678-695 (2007).
M. Takahashi et al., "Research regarding pyrethrin biosynthesis in pyrethrum flowers: Acyl-CoA transferase contributing Ester bonding." Collection in summarized lecture in agricultural chemical society of Japan ABSJ in 2006.
Rivera et al., "Chrysanthemyl Diphosphate Synthase: Isolation of the Gene and Characterization of the Recombinant Non-Head-to-Tail Monoterpene Synthase from *Chrysanthemum cinerariaefolium*," PNAS, vol. 98, No. 8, pp. 4373-4378, Apr. 10, 2001.
"Natural Pyrethrins," Mass Meeting of Agricultural Chemical Scientific Society, Mar. 5, 2004.
Matsuda et al., "Biosynthesis of Pyrethrin I in Seedlings of *Chrysanthemum cinerariaefolium*," Phytochemistry, vol. 66, pp. 1529-1535, 2005.
Hitmi et al., "The Production of Pyrethrins by Plant Cell and Tissue Cultures of *Chrysanthemum cinerariaefolium* and Tagetes Species," Critical Reviews in Biochemistry and Molecular Biology, vol. 35, No. 5, pp. 317-337, 2000.
Crombie, "Chemistry and Biosynthesis of Natural Pyrethrin," Pestic. Sci., vol. 11, pp. 102-118, 1980.

* cited by examiner

*Primary Examiner* — Rebecca Prouty
*Assistant Examiner* — Todd M Epstein
(74) *Attorney, Agent, or Firm* — Oliff, PLC (57) ABSTRACT

Amino acid sequences of an enzyme involved in pyrethrin biosynthesis and a base sequence of the gene thereof; constructing vectors bearing the gene and transformants; and extractable from plant bodies producing pyrethrin by applying such creative techniques to plant bodies with faster growth aiming to provide a method to efficiently produce pyrethrin. A gene encoding a protein consisting of the amino acid sequence of SEQ ID NO: 1. A protein consisting of the amino acid sequence of SEQ ID NO: 2.

4 Claims, 6 Drawing Sheets

FIGURE 1

(a) SEQ ID NO:1

MAVASSKRGALVLVAVLCLSLPTGCLSSQQAAALFIFGDSVFDPGNNNHINTHVNFKA
NFWPYGQSYFSSPTGRFSDGRIIPDFIAEYASLPIIPAYLEPNNDFTHGANFASAGAGA
LIASHAGLAVGLQTQLHYFGDLVDHYRQNLGDIKSRQLLSDAVYLFSCGGNDYQSPY
YPYTQEQYVDIVIGNMTNVIKGIYEKGGRKFGVVNVPLIGCWPGMRAKQPGNACNT
EVDELTRLHNQAFAKTLEHLEKQLEGFVYAKFDLSTAILNRMKNPSKYGFKEGESAC
CGSGPFGGNYDCGRIKEFGLCDNATEYFFFDPFHPNELASRQFAEMFWDGDSMVTQ
PYNLKALFEGKPSTKYLPNDEL (b) SEQ ID NO:2

MKIEEGKLVIWINGDKGYNGLAEVGKKFEKDTGIKVTVEHPDKLEEKFPQVAATGDGPDIIFWAHDRF
GGYAQSGLLAEITPDKAFQDKLYPFTWDAVRYNGKLIAYPIAVEALSLIYNKDLLPNPPKTWEEIPALDK
ELKAKGKSALMFNLQEPYFTWPLIAADGGYAFKYENGKYDIKDVGVDNAGAKAGLTFLVDLIKNKHM
NADTDYSIAEAAFNKGETAMTINGPWAWSNIDTSKVNYGVTVLPTFKGQPSKPFVGVLSAGINAASP
NKELAKEFLENYLLTDEGLEAVNKDKPLGAVALKSYEEELVKDPRIAATMENAQKGEIMPNIPQMSAF
WYAVRTAVINAASGRQTVDEALKDAQTNSSSNNNNNNNNNLGDDDDKVPEFLEVLFQGPSQQAA
ALFIFGDSVFDPGNNNHINTHVNFKANFWPYGQSYFSSPTGRFSDGRIIPDFIAEYASLPIIPAYLEPNND
FTHGANFASAGAGALIASHAGLAVGLQTQLRYFGDLVDHYRQNLGDIKSRQLLSDAVYLFSCGGNDYQ
SPYYPYTQEQYVDIVIGNMTNVIKGIYEKGGRKFGVVNVPLIGCWPGMRAKQPGNTCNTEVDELTRL
HNQAFAKRLEQLEKQLEGFVYAKFDLSTAILNRMKNPSKYGFKEGESACCGSGPFGGNYDCGRIKEFGL
CDNATEYFFFDPFHPNELASRQFAEMFWDGDSMVTQPYNLKALFEGKPSTKYLPNDEL

FIGURE 2

SEQ ID NO: 5

TTAAACGGGATGTCCAAAGWCATTTAACTTCCACTAGCAAGTTAGAGCATTTTTCAC
ACCTCTTGATCTGAGCACATATAAGCTATGGCTGTTGCAAGCAGCAAWCGGGGTGC
TCTTGTTTTGGTTGCTGTTTTGTGTCTTTCACTACCTACAGGTTGCCTGAGTTCTCAA
CAAGCTGCTGCACTATTTATATTTGGTGATTCGGTTTTCGATCCTGGTAACAATAACC
ACATCAACACCCATGTTAATTTTAAAGCGAACTTTTGGCCATATGGTCAATCCTACTT
CAGTTCACCAACTGGTAGATTCTCTGATGGCCGTATCATCCCTGATTTCATTGCTGAG
TATGCAAGTCTGCCTATCATTCCTGCGTATCTCGAGCCAAACAATGATTTTACGCATG
GAGCMAACTTTGCGTCAGCAGGAGCCGGTGCCTTGATTGCCTCCCATGCTGGACTT
GCAGTTGGCCTTCAAACACAACTACATTACTTTGGCGATTTAGTAGACCATTATCGG
CAGAATTTAGGTGATATTAAATCTAGGCAGCTACTATCCGATGCTGTCTACTTGTTTA
GCTGTGGAGGTAACGACTACCAAAGCCCTTACTATCCATATACTCAAGAGCAATACG
TGGACATTGTGATTGGAAACATGACTAACGTCATCAAGGGAATATACGAAAAAGGT
GGAAGAAAATTTGGGGTTGTGAATGTCCCGCTTATAGGCTGTTGGCCGGGAATGCG
AGCAAAACAACCTGGAAATGCTTGCAACACAGAGGTCGATGAACTTACTAGACTAC
ACAATCAAGCATTTGCAAAAACACTAGAACATTTGGAGAAACAGTTGGAAGGCTTT
GTGTATGCTAAATTCCATCTTTCAACTGCCATTCTCAATAGAATGAAGAACCCCTCAA
AATATGGTTTTAAGGAAGGCGAGAGCGCATGTTGCGGTAGTGGTCCTTTTGGAGGG
AATTATGATTGTGGCAGAATAAAAGAGTTTGGACTATGTGATAATGCAACTGAGTA
TTTTTTCTTTGACCCTTTTCATCCTAATGAATTGGCGAGTCGCCAATTTGCAGAGATG
TTTTGGGATGGGGATTCCATGGTCACACAGCCTTACAATTTGAAAGCACTCTTTGAA
GGGAAGCCATCAACAAAATATCTCCCAAATGATGAGCTCTAATGTAGAGCATGTTGA
CTCGGTTCTTTCTCCATGATCGARCCATTAGCAAAATAATAATATGAGGTCACACTAG
CAACATAATGGAATGATCTTAATAATGCCATGGTCTTCTTCATGATTGTTCCGTCTTT
TTAGTTTGACTTTTTTATTTGATCTTGTTGAACCGAATCAAGGGACTTTTGATGACCA
TGATTCGATTCATATTCTTTAGTTGTCATGTTGGCTTTAAAAAACTATCTACGTATGT
CAATGTAGCAACTTCTGGTTATTAAAAAAAAAAAAAAAAAAAAAAAAAAA

FIGURE 3

[Structure of pyrethrins]

| | Side chain of chrysanthemic acid moiety (R₁) | Side chain of rethrolone moiety (R₂) |
|---|---|---|
| Pyrethrin I | -CH₃ | -CH=CH₂ |
| Pyrethrin II | -COOCH3 | -CH=CH₂ |
| Cinerin I | -CH₃ | -CH₃ |
| Cinerin II | -COOCH₃ | -CH₃ |
| Jasmolin I | -CH₃ | -CH₂CH₃ |
| Jasmolin II | -COOCH₃ | -CH₂CH₃ |

Chrysanthemic acid moiety    Rethrolone moiety

FIGURE 4

[Biosynthesis reaction of ester by acyltransferase]

R-CO-S-CoA + R'-OH    →    R-COO-R' + CoA-SH

Acyltransferase

FIGURE 5

[Biosynthesis reaction of pyrethrin]

(1R)-trans Chrysanthemoyl CoA    (S)-Pyrethrolone    Chrysanthemoyl group transferase    Pyrethrin I

FIGURE 6

[Examples of HPLC analysis results of pyrethrin-biosynthesis reaction solution]

(a) Fraction without enzyme activity   (b) Fraction with enzyme activity

FIGURE 7

[Flow of enzyme purification from plant bodies]

Preparation of crude enzyme solution
↓
Fractionation by ammonium sulfate precipitation
↓
Crude purification by batch method using Phenyl Sepharose
↓
Anion Exchange Chromathography (Q Sepharose)
↓
Hydrophobic Chromathography (Phenyl Superose)
↓
Gel Filtration (Superdex 75)

FIGURE 8

Electrophoresis (SDS-PAGE) photo image of purified pyrethrin biosynthetic enzyme

FIGURE 9

(a) SEQ ID NO: 6

SQQAAALFIFGDSVFDPGNNNHINTHVNFKANF (b) SEQ ID NO: 7

QNLGDIK (c) SEQ ID NO: 8

QLEGFVYAK

SEQUENCE LISTING

<160> NUMBER OF SEQ ID NOS: 10

<210> SEQ ID NO 1
<211> LENGTH: 365
<212> TYPE: PRT
<213> ORGANISM: Pyrethrum Cinerariifolium

<400> SEQUENCE: 1

```
Met Ala Val Ala Ser Ser Lys Arg Gly Ala Leu Val Leu Val Ala Val
1               5                   10                  15

Leu Cys Leu Ser Leu Pro Thr Gly Cys Leu Ser Gln Gln Ala Ala
            20                  25                  30

Ala Leu Phe Ile Phe Gly Asp Ser Val Phe Asp Pro Gly Asn Asn Asn
            35                  40                  45

His Ile Asn Thr His Val Asn Phe Lys Ala Asn Phe Trp Pro Tyr Gly
        50                  55                  60

Gln Ser Tyr Phe Ser Ser Pro Thr Gly Arg Phe Ser Asp Gly Arg Ile
65                  70                  75                  80

Ile Pro Asp Phe Ile Ala Glu Tyr Ala Ser Leu Pro Ile Ile Pro Ala
                85                  90                  95

Tyr Leu Glu Pro Asn Asn Asp Phe Thr His Gly Ala Asn Phe Ala Ser
            100                 105                 110

Ala Gly Ala Gly Ala Leu Ile Ala Ser His Ala Gly Leu Ala Val Gly
        115                 120                 125

Leu Gln Thr Gln Leu His Tyr Phe Gly Asp Leu Val Asp His Tyr Arg
    130                 135                 140

Gln Asn Leu Gly Asp Ile Lys Ser Arg Gln Leu Leu Ser Asp Ala Val
145                 150                 155                 160

Tyr Leu Phe Ser Cys Gly Gly Asn Asp Tyr Gln Ser Pro Tyr Tyr Pro
                165                 170                 175

Tyr Thr Gln Glu Gln Tyr Val Asp Ile Val Ile Gly Asn Met Thr Asn
            180                 185                 190

Val Ile Lys Gly Ile Tyr Glu Lys Gly Arg Lys Phe Gly Val Val
        195                 200                 205

Asn Val Pro Leu Ile Gly Cys Trp Pro Gly Met Arg Ala Lys Gln Pro
    210                 215                 220

Gly Asn Ala Cys Asn Thr Glu Val Asp Glu Leu Thr Arg Leu His Asn
225                 230                 235                 240

Gln Ala Phe Ala Lys Thr Leu Glu His Leu Glu Lys Gln Leu Glu Gly
                245                 250                 255

Phe Val Tyr Ala Lys Phe Asp Leu Ser Thr Ala Ile Leu Asn Arg Met
            260                 265                 270

Lys Asn Pro Ser Lys Tyr Gly Phe Lys Glu Gly Glu Ser Ala Cys Cys
        275                 280                 285

Gly Ser Gly Pro Phe Gly Gly Asn Tyr Asp Cys Gly Arg Ile Lys Glu
    290                 295                 300

Phe Gly Leu Cys Asp Asn Ala Thr Glu Tyr Phe Phe Asp Pro Phe
305                 310                 315                 320

His Pro Asn Glu Leu Ala Ser Arg Gln Phe Ala Glu Met Phe Trp Asp
                325                 330                 335

Gly Asp Ser Met Val Thr Gln Pro Tyr Asn Leu Lys Ala Leu Phe Glu
            340                 345                 350

Gly Lys Pro Ser Thr Lys Tyr Leu Pro Asn Asp Glu Leu
        355                 360                 365
```

<210> SEQ ID NO 2
<211> LENGTH: 738
<212> TYPE: PRT
<213> ORGANISM: Pyrethrum Cinerariifolium

<400> SEQUENCE: 2

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Asp
        370                 375                 380
```

Asp Asp Asp Lys Val Pro Glu Phe Leu Glu Val Leu Phe Gln Gly Pro
385                 390                 395                 400

Ser Gln Gln Ala Ala Ala Leu Phe Ile Phe Gly Asp Ser Val Phe Asp
                405                 410                 415

Pro Gly Asn Asn Asn His Ile Asn Thr His Val Asn Phe Lys Ala Asn
            420                 425                 430

Phe Trp Pro Tyr Gly Gln Ser Tyr Phe Ser Ser Pro Thr Gly Arg Phe
        435                 440                 445

Ser Asp Gly Arg Ile Ile Pro Asp Phe Ile Ala Glu Tyr Ala Ser Leu
    450                 455                 460

Pro Ile Ile Pro Ala Tyr Leu Glu Pro Asn Asn Asp Phe Thr His Gly
465                 470                 475                 480

Ala Asn Phe Ala Ser Ala Gly Ala Gly Ala Leu Ile Ala Ser His Ala
                485                 490                 495

Gly Leu Ala Val Gly Leu Gln Thr Gln Leu Arg Tyr Phe Gly Asp Leu
            500                 505                 510

Val Asp His Tyr Arg Gln Asn Leu Gly Asp Ile Lys Ser Arg Gln Leu
        515                 520                 525

Leu Ser Asp Ala Val Tyr Leu Phe Ser Cys Gly Gly Asn Asp Tyr Gln
    530                 535                 540

Ser Pro Tyr Tyr Pro Tyr Thr Gln Glu Gln Tyr Val Asp Ile Val Ile
545                 550                 555                 560

Gly Asn Met Thr Asn Val Ile Lys Gly Ile Tyr Glu Lys Gly Gly Arg
                565                 570                 575

Lys Phe Gly Val Val Asn Val Pro Leu Ile Gly Cys Trp Pro Gly Met
            580                 585                 590

Arg Ala Lys Gln Pro Gly Asn Thr Cys Asn Thr Glu Val Asp Glu Leu
        595                 600                 605

Thr Arg Leu His Asn Gln Ala Phe Ala Lys Arg Leu Glu Gln Leu Glu
    610                 615                 620

Lys Gln Leu Glu Gly Phe Val Tyr Ala Lys Phe Asp Leu Ser Thr Ala
625                 630                 635                 640

Ile Leu Asn Arg Met Lys Asn Pro Ser Lys Tyr Gly Phe Lys Glu Gly
                645                 650                 655

Glu Ser Ala Cys Cys Gly Ser Gly Pro Phe Gly Gly Asn Tyr Asp Cys
            660                 665                 670

Gly Arg Ile Lys Glu Phe Gly Leu Cys Asp Asn Ala Thr Glu Tyr Phe
        675                 680                 685

Phe Phe Asp Pro Phe His Pro Asn Glu Leu Ala Ser Arg Gln Phe Ala
690                 695                 700

Glu Met Phe Trp Asp Gly Asp Ser Met Val Thr Gln Pro Tyr Asn Leu
705                 710                 715                 720

Lys Ala Leu Phe Glu Gly Lys Pro Ser Thr Lys Tyr Leu Pro Asn Asp
                725                 730                 735

Glu Leu

<210> SEQ ID NO 3
<211> LENGTH: 1098
<212> TYPE: DNA
<213> ORGANISM: Pyrethrum Cinerariifolium

<400> SEQUENCE: 3
atggctgttg caagcagcaa wcggggtgct cttgttttgg ttgctgtttt gtgtctttca      60
ctacctacag gttgcctgag ttctcaacaa gctgctgcac tatttatatt tggtgattcg     120

```
gttttcgatc ctggtaacaa taaccacatc aacacccatg ttaattttaa agcgaacttt      180
tggccatatg gtcaatccta cttcagttca ccaactggta gattctctga tggccgtatc      240
atccctgatt tcattgctga gtatgcaagt ctgcctatca ttcctgcgta tctcgagcca      300
aacaatgatt ttacgcatgg agcmaacttt gcgtcagcag gagccggtgc cttgattgcc      360
tcccatgctg gacttgcagt tggccttcaa acacaactac attactttgg cgatttagta      420
gaccattatc ggcagaattt aggtgatatt aaatctaggc agctactatc cgatgctgtc      480
tacttgttta gctgtggagg taacgactac caaagccctt actatccata tactcaagag      540
caatacgtgg acattgtgat tggaaacatg actaacgtca tcaagggaat atacgaaaaa      600
ggtggaagaa aatttgggt tgtgaatgtc ccgcttatag gctgttggcc gggaatgcga      660
gcaaaacaac ctggaaatgc ttgcaacaca gaggtcgatg aacttactag actacacaat      720
caagcatttg caaaaacact agaacatttg gagaaacagt tggaaggctt tgtgtatgct      780
aaattcgatc tttcaactgc cattctcaat agaatgaaga acccctcaaa atatggtttt      840
aaggaaggcg agagcgcatg ttgcggtagt ggtccttttg gagggaatta tgattgtggc      900
agaataaaag agtttggact atgtgataat gcaactgagt attttttctt tgaccctttt      960
catcctaatg aattggcgag tcgccaattt gcagagatgt tttgggatgg ggattccatg     1020
gtcacacagc cttacaaatt tgaaagcactc tttgaaggga agccatcaac aaaatatctc     1080
ccaaatgatg agctctaa                                                   1098

<210> SEQ ID NO 4
<211> LENGTH: 2217
<212> TYPE: DNA
<213> ORGANISM: Pyrethrum Cinerariifolium

<400> SEQUENCE: 4
atgaaaatcg aagaaggtaa actggtaatc tggattaacg gcgataaagg ctataacggt       60
ctcgctgaag tcggtaagaa attcgagaaa gataccggaa ttaaagtcac cgttgagcat      120
ccggataaac tggaagagaa attcccacag gttgcggcaa ctggcgatgg ccctgacatt      180
atcttctggg cacacgaccg cttttggtggc tacgctcaat ctggcctgtt ggctgaaatc      240
accccggaca aagcgttcca ggacaagctg tatccgtttta cctgggatgc cgtacgttac      300
aacggcaagc tgattgctta cccgatcgct gttgaagcgt tatcgctgat ttataacaaa      360
gatctgctgc cgaacccgcc aaaaaccctgg gaagagatcc cggcgctgga taagaactg      420 aaagcgaaag gtaagagcgc gctgatgttc aacctgcaag aaccgtactt cacctggccg      480
ctgattgctg ctgacggggg ttatgcgttc aagtatgaaa acggcaagta cgacattaaa      540 gacgtggcg tggataacgc tggcgcgaaa gcgggtctga ccttcctggt tgacctgatt      600
aaaaacaaac acatgaatgc agacaccgat tactccatcg cagaagctgc ctttaataaa      660
ggcgaaacag cgatgaccat caacgggcccg tgggcatggt ccaacatcga caccagcaaa      720
gtgaattatg gtgtaacggt actgccgacc ttcaagggtc aaccatccaa accgttcgtt      780
ggcgtgctga gcgcaggtat taacgccgcc agtccgaaca aagagctggc aaaagagttc      840
ctcgaaaact atctgctgac tgatgaaggt ctggaagcgg ttaataaaga caaaccgctg      900
ggtgccgtag cgctgaagtc ttacgaggaa gagttggtga agatccgcg gattgccgcc      960 actatgaaaa acgcccagaa aggtgaaatc atgccgaaca tcccgcagat gtccgctttc     1020
tggtatgccg tgcgtactgc ggtgataaac gccgccagcg tcgtcagac tgtcgatgaa     1080 gccctgaaag acgcgcagac taattcgagc tcgaacaaca caacaataa caataacaac     1140
```

```
aacctcgggg atgacgatga caaggtaccg gaattcctgg aagttctgtt ccagggccc     1200 tctcaacaag ctgctgcact atttatattt ggtgattcgg ttttcgatcc tggtaacaat    1260
aaccacatca acacccatgt taattttaaa gcgaacttt ggccatatgg tcaatcctac     1320
ttcagttcac caactggtag attctctgat ggccgtatca tccctgattt cattgctgag    1380
tatgcaagtc tgcctatcat tcctgcgtat ctcgagccaa acaatgattt tacgcatgga    1440
gccaactttg cgtcagcagg agctggtgcc ttgattgcct cccatgctgg acttgcagtt    1500
ggccttcaaa cacaactacg ttactttggc gatttagtag accattatcg gcagaattta    1560
ggtgatatta atctaggca gctactatcc gatgctgtct acttgtttag ctgtggaggt     1620
aacgactacc aaagcccta ctatccatat actcaagagc aatacgtgga cattgtgatt     1680
ggaaacatga ctaacgtcat caagggaata tacgaaaaag gtggaagaaa atttggtgtt    1740
gtgaatgtcc cgcttatagg ctgttggccg ggaatgcgag caaaacaacc tggaaatact    1800
tgcaacacag aggtcgatga acttactaga ctacacaatc aagcatttgc aaaaagacta    1860
gaacaattgg agaaacagtt ggaaggcttt gtgtatgcta aattcgatct ttcaactgcc    1920
attctcaata gaatgaagaa cccctcaaaa tatggtttta aggaaggcga gagcgcatgt    1980
tgcggtagtg gtccttttgg agggaattat gattgtggca gaataaaaga gtttggacta    2040
tgtgataatg caactgagta ttttttcttt gacccttttc atcctaatga attggcgagt    2100
cgccaatttg cagagatgtt tgggatggg gattccatgg tcacacagcc ttacaatttg    2160
aaagcactct ttgaagggaa gccatcaaca aaatatctcc caaatgatga gctctaa      2217

<210> SEQ ID NO 5
<211> LENGTH: 1479
<212> TYPE: DNA
<213> ORGANISM: Pyrethrum Cinerariifolium

<400> SEQUENCE: 5
ttaaacggga tgtccaaagw catttaactt ccactagcaa gttagagcat ttttcacacc     60
tcttgatctg agcacatata agctatggct gttgcaagca gcaawcgggg tgctcttgtt    120
ttggttgctg ttttgtgtct ttcactacct acaggttgcc tgagttctca acaagctgct    180
gcactattta tatttggtga ttcggttttc gatcctggta acaataacca catcaacacc    240
catgttaatt ttaaagcgaa cttttggcca tatggtcaat cctacttcag ttcaccaact    300
ggtagattct ctgatggccg tatcatccct gatttcattg ctgagtatgc aagtctgcct    360
atcattcctg cgtatctcga gccaaacaat gattttacgc atggagcmaa ctttgcgtca    420
gcaggagccg gtgccttgat tgcctcccat gctggacttg cagttggcct tcaaacacaa    480
ctacattact ttggcgattt agtagaccat tatcggcaga atttaggtga tattaaatct    540
aggcagctac tatccgatgc tgtctacttg tttagctgtg gaggtaacga ctaccaaagc    600
ccttactatc catatactca agagcaatac gtggacattg tgattggaaa catgactaac    660
gtcatcaagg gaatatacga aaaggtgga agaaaatttg gggttgtgaa tgtcccgctt    720
ataggctgtt ggccgggaat gcgagcaaaa caacctggaa atgcttgcaa cacagaggtc    780
gatgaactta ctagactaca caatcaagca tttgcaaaaa cactagaaca tttggagaaa    840
cagttggaag ctttgtgta tgctaaattc gatctttcaa ctgccattct caatagaatg    900
aagaacccct caaaatatgg ttttaaggaa ggcgagagcg catgttgcgg tagtggtcct    960
tttgagggga attatgattg tggcagaata aaagagtttg gactatgtga taatgcaact    1020
gagtattttt tctttgaccc ttttcatcct aatgaattgg cgagtcgcca atttgcagag    1080
```

```
atgttttggg atggggattc catggtcaca cagccttaca atttgaaagc actctttgaa    1140
gggaagccat caacaaaata tctcccaaat gatgagctct aatgtagagc atgttgactc    1200
ggttctttct ccatgatcga rccattagca aaataataat atgaggtcac actagcaaca    1260
taatggaatg atcttaataa tgccatggtc ttcttcatga ttgttccgtc ttttagttt     1320 gactttttta tttgatcttg ttgaaccgaa tcaagggact tttgatgacc atgattcgat    1380
tcatattctt tagttgtcat gttggcttta aaaaactatc tacgtatgtc aatgtagcaa    1440
cttctggtta ttaaaaaaaa aaaaaaaaaa aaaaaaaa                            1479
```

```
<210> SEQ ID NO 6
<211> LENGTH: 33
<212> TYPE: PRT
<213> ORGANISM: Pyrethrum Cinerariifolium

<400> SEQUENCE: 6

Ser Gln Gln Ala Ala Ala Leu Phe Ile Phe Gly Asp Ser Val Phe Asp
1               5                   10                  15

Pro Gly Asn Asn Asn His Ile Asn Thr His Val Asn Phe Lys Ala Asn
            20                  25                  30

Phe

<210> SEQ ID NO 7
<211> LENGTH: 7
<212> TYPE: PRT
<213> ORGANISM: Pyrethrum Cinerariifolium

<400> SEQUENCE: 7

Gln Asn Leu Gly Asp Ile Lys
1               5

<210> SEQ ID NO 8
<211> LENGTH: 9
<212> TYPE: PRT
<213> ORGANISM: Pyrethrum Cinerariifolium

<400> SEQUENCE: 8

Gln Leu Glu Gly Phe Val Tyr Ala Lys
1               5

<210> SEQ ID NO 9
<211> LENGTH: 53
<212> TYPE: DNA
<213> ORGANISM: Artificial Sequence
<220> FEATURE:
<223> OTHER INFORMATION: Synthetic Construct: Primer

<400> SEQUENCE: 9
ccggaattcc tggaagttct gttccagggg ccctctcaac aagctgctgc act           53

<210> SEQ ID NO 10
<211> LENGTH: 29
<212> TYPE: DNA
<213> ORGANISM: Artificial Sequence
<220> FEATURE:
<223> OTHER INFORMATION: Synthetic Construct: Primer

<400> SEQUENCE: 10
cccaagcttt agagctcatc atttgggag                                      29
```

PROTEIN EXHIBITING ACTIVITY OF PYRETHRIN BIOSYNTHETIC ENZYME, GENE ENCODING THE PROTEIN, AND VECTOR BEARING THE GENE

This is a Continuation-in-Part of application Ser. No. 13/137,327 filed Aug. 5, 2011, which in turn is a Continuation-in-Part of application Ser. No. 12/457,193 filed Jun. 3, 2009, now U.S. Pat. No. 8,129,180, and claims the benefit of Japanese Application No. 2008-208295 filed Aug. 13, 2008. The disclosure of the prior applications is hereby incorporated by reference herein in its entirety.

BACKGROUND

The present invention relates to a protein exhibiting activity of a pyrethrin biosynthetic enzyme, a gene encoding thereof, and vector bearing the gene.

Pyrethrin, which is a secondary metabolite contained in pyrethrum, exhibits excellent insecticidal activity against insects as well as being an ideal feature as an insecticidal constituent where toxicity against mammals is low, and is widely used for mosquito coils, and insecticide sprays and powders. Recently, demand for pyrethrin has decreased because of the remarkable development of synthetic pyrethroid. However, pyrethrin still has a high utility value as a plant-derived, and environmentally friendly material for insecticides, and further investigation has continued to a point where pyrethrin can be obtained inexpensively and effectively. In particular, the existence value of the above pyrethrin, a secondary metabolite, has been emphasized again, because of increasing oil prices, which is a raw material of synthetic pyrethroid, and the like.

Pyrethrin is mainly extracted from the flower part of pyrethrum. However, the growth duration of pyrethrum until flowering is very long, over three years. It is considered that selection and breeding of high-producing strains of pyrethrum and promotion of pyrethrin biosynthesis in plant cells of the same or different species have a beneficial effect as a means for increasing the efficiency of pyrethrin production.

Figure 3:
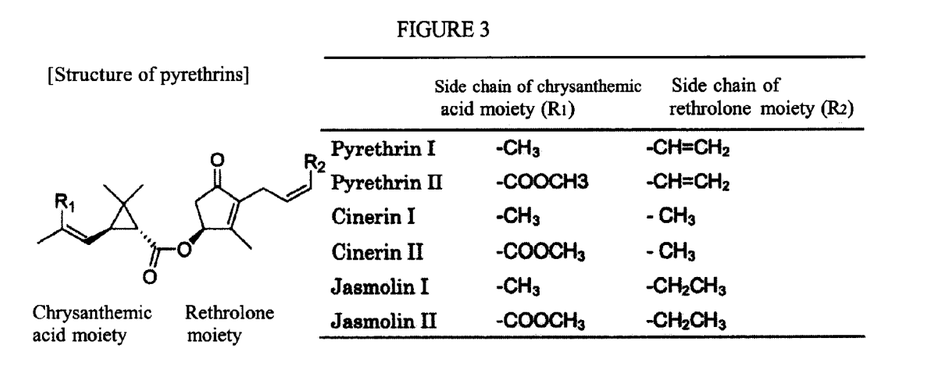
FIG. 3 shows a general chemical formula for pyrethrins and a list of the side chain structures of chrysanthemic acid moiety (R1) and rethrolone moiety (R2).

Pyrethrin has an ester-bonded structure between chrysanthemic acid that is a monoterpene carboxylic acid and rethrolones (alcohols), which is a metabolite of fatty acid oxidation (FIG. 3). It is known that in biosynthesis of pyrethrin, chrysanthemic acid and rethrolones are biosynthesized in different metabolic pathways and an ester binding is eventually formed therebetween.

Methods for increasing efficiency of the above-described biosynthesis of pyrethrin include use of genes involved in the biosynthesis. In order to implement biosynthesis of pyrethrin, isolation and identification of the relevant gene is crucial.

Figure 4:
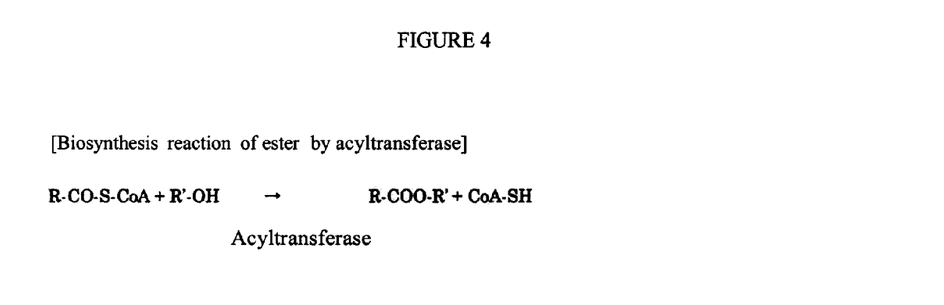
FIG. 4 depicts a general chemical reaction for the biosynthesis of ester compounds in plant cells catalyzed by acyltransferase using CoA thioester of carboxylic acid (acyl-CoA, RCO—S-CoA) and alcohol (R'—OH) as substrates.
Figure 5:
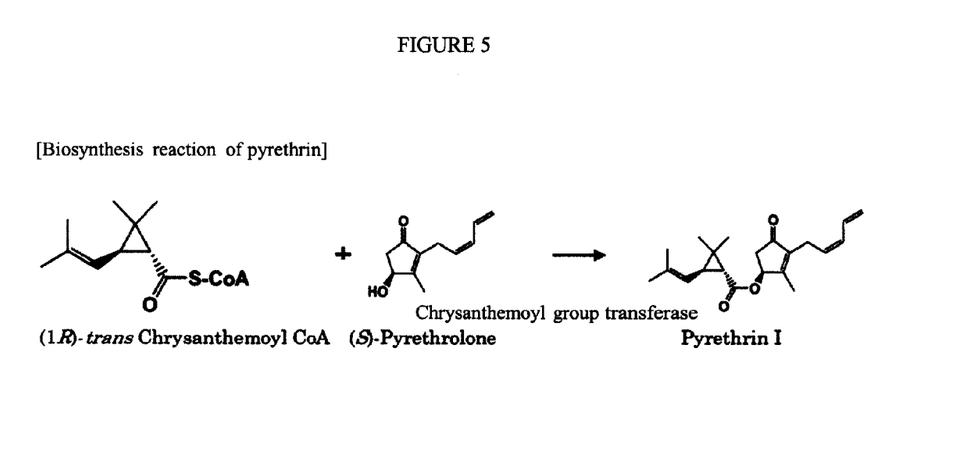
FIG. 5 depicts a reaction formula showing an illustrative example of a pyrethrin biosynthetic reaction catalyzed by chrysanthemoyl group transferase.

Meanwhile, various ester compounds produced by plant cells are biosynthesized by catalysis of acyltransferase from CoA thioester of carboxylic acid (acyl-CoA, RCO—S-CoA) and alcohol (R'—OH) as substrates (FIG. 4), and these biosyntheses are described, for example, in Non-Patent Document 1 and 2.

As an example of such acyltransferase in the pyrethrin biosynthesis, existence of chrysanthemoyl/pyrethroyl transferase (pyrethrin biosynthetic enzyme) which uses (1R)-trans-chrysanthemoyl-CoA and (S)-pyrethrolone as substrates have been predicted, however, there has been no isolated and specific composition based on an amino acid sequence, and naturally a gene encoding the protein based on such an amino acid sequence is not particularly sought.

Meanwhile, Japanese Patent Application Publication No. H9-504684 discloses an amino acid sequence of chrysanthemyl diphosphate synthase, an enzyme that can catalyze synthesis of chrysanthemyl diphosphate, which is adopted as a raw material for chemical synthesis of pyrethrin, and a sequence of a gene coding a protein based on such an amino acid sequence. However, there has been neither disclosure nor suggestion about the gene encoding the enzyme per se, which can catalyze the above pyrethrin biosynthesis, and the gene coding protein based on such an amino acid sequence. As obvious from the situation in the conventional art, elucidation of the gene encoding the above enzyme protein through identification of the enzyme involved in the pyrethrin biosynthesis, and effective biosynthesis of pyrethrin based on knowledge of genetic engineering have not been achieved.

Patent Document 1: Japanese Patent Application Publication No. H9-504684

Non-Patent Document 1: R. Kalscheuer and A. Steinbuchel, "A novel bifunctional wax ester synthase/acyl-CoA:diacylglycerol acyltransferase mediates wax ester and triacylglycerol biosynthesis in *Acinetobacter* calcoaceticus ADP1," J. Biol. Chem. 278:8075-8082 (2003).

Non-Patent Document 2: J. Luo et al., "Convergent evolution in the BAHD family of acyl transferases: identification and characterization of anthocyanin acyl transferases from *Arabidopsis thaliana*," Plant J. 50:678-695 (2007).

SUMMARY

The present invention aims to determine amino acid sequences of the enzyme involved in pyrethrin biosynthesis and a base sequence of the gene thereof, and to construct vectors bearing the gene and transformants, as well as to provide methods for effectively producing pyrethrin by applying such creative techniques to plants with faster growth.

In order to solve the above issues, the inventors of the present invention purified a pyrethrin synthesis enzyme protein by using the pyrethrum flower as a raw material and pyrethrin I synthesis activity as an indicator, and by performing crude fractionation of a protein and crude purification by batch method using hydrophobic resin, and then purification with a predetermined combination of chromatography; and finally analyzed an internal amino acid sequence and amino terminal sequence of the relevant protein as is described below. RACE-PCR was performed and a polynucleotide fragment of an unknown part of the sequence was amplified using a cDNA library obtained from a flower part of pyrethrum as temperate and degenerate primers designed based on crude amino acid sequences, which have been clarified through the above analysis.

Figure 1:
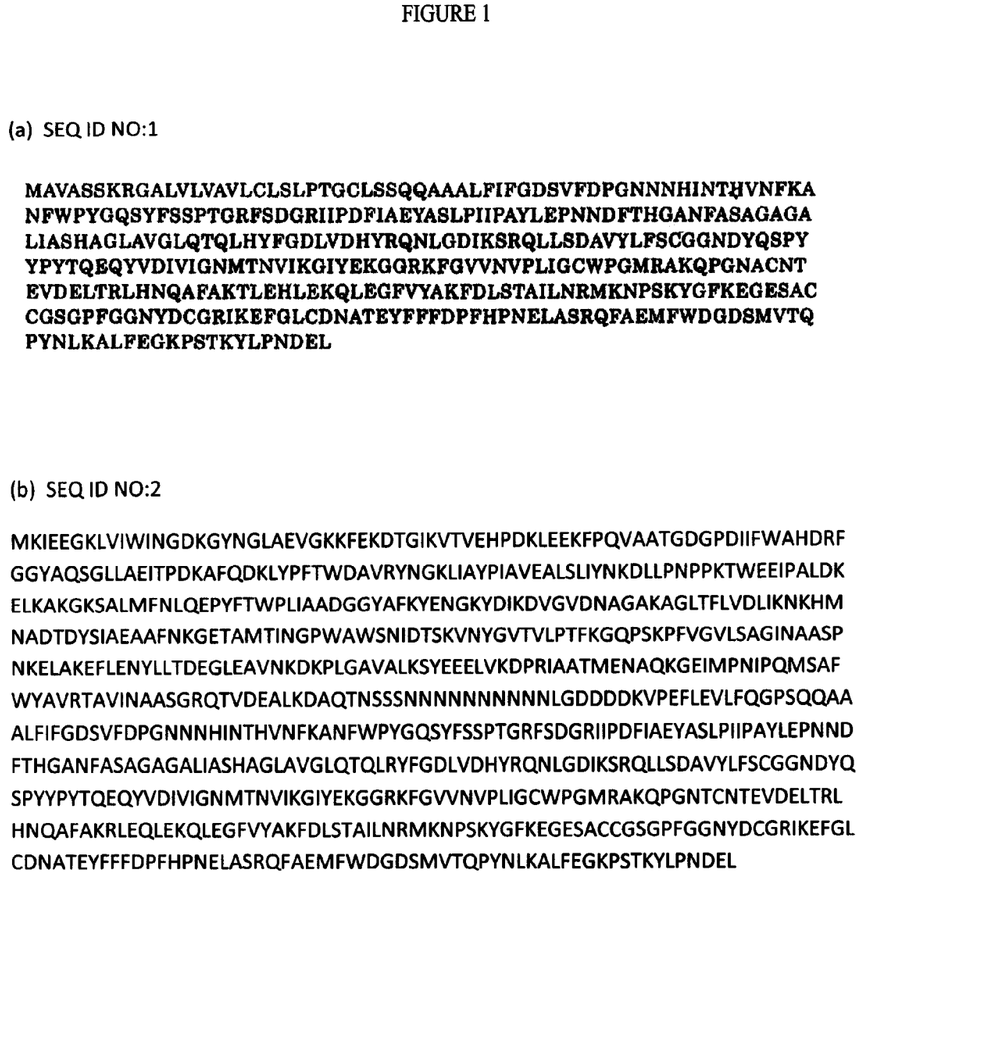
FIG. 1 shows an illustrative example of an amino acid sequence of a pyrethrin biosynthetic enzyme of the present invention.
Figure 2:
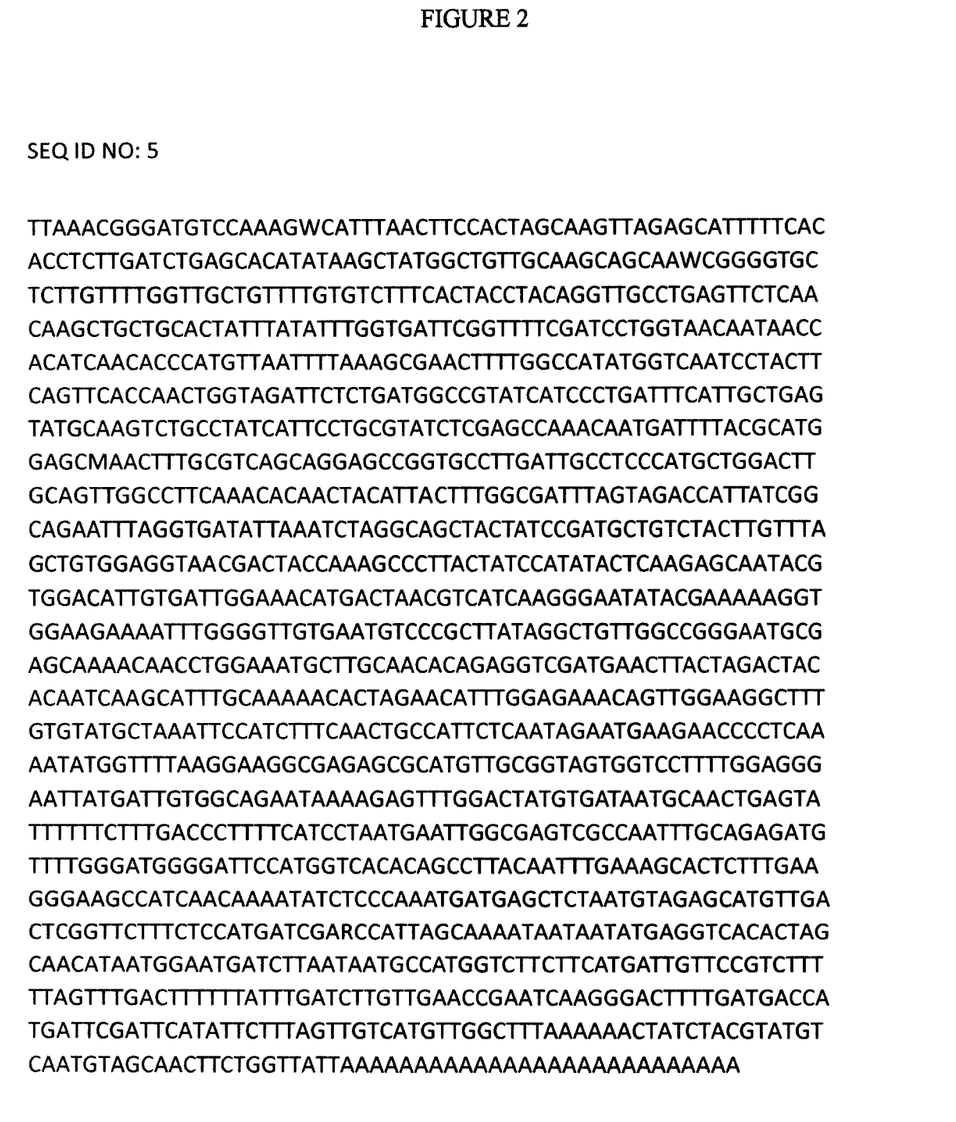
FIG. 2 shows sequence of a gene encoding the protein of the amino acid sequence of FIG. 1(a) corresponding to a figure showing a base sequence of SEQ ID NO: 5.

An amplified polynucleotide fragment of the base sequence was analyzed with a DNA sequencer. As a result, a full length gene of a coding sequence ("CDS") of a pyrethrin biosynthetic enzyme, including the base sequence shown in FIG. 2, i.e., SEQ ID NO:5, and an amino acid sequence encoded by the gene as shown in FIG. 1(*a*), i.e., SEQ ID NO: 1 and the sequence shown in FIG. 1(*b*), i.e., SEQ ID NO:2, were determined. The present invention was completed based on such determination of the sequences.

Embodiments of the present invention include the following:

(1) A pyrethrin biosynthetic enzyme, produced by a method comprising the sequential steps of:

obtaining a raw material from a pyrethrum flower;

obtaining from the raw material a precipitate of a crude protein fractionation with ammonium sulfate precipitation;

crudely purifying the precipitate by a batch method using a hydrophobic resin;

purifying the enzyme solution obtained by crude purification with anion-exchange chromatography;

purifying with hydrophobic chromatography;

purifying with gel filtration to obtain an enzyme protein with a molecular weight of approximately 40,000; and transforming an initial part of the enzyme protein into maltose binding protein sequence, wherein the transformed enzyme protein has a molecular weight of approximately 80,000.

(2) A protein consisting of the amino acid sequence set forth in SEQ ID NO: 2.

(3) A gene encoding a protein consisting of the amino acid sequence set forth in SEQ ID NO: 2.

(4) A vector comprising the gene according to (3).

BRIEF DESCRIPTION OF THE DRAWINGS

FIG. 1(a) shows a typical example of an enzyme obtained from a pyrethrum flower (SEQ ID NO:1), and FIG. 1(b) depicts SEQ ID NO: 2, which is an illustrative example of the signal sequence transformed at the initial part of SEQ ID NO: 1 shown in FIG. 1(a).

FIGS. 6(a) and 6(b) show examples without and with enzyme activity at a protein purification step, respectively.

FIG. 9(a) shows the amino acid sequence of SEQ ID NO: 6, FIG. 9(b) shows the amino acid sequence of SEQ ID NO: 7, and FIG. 9(c) shows the amino acid sequence of SEQ ID NO: 8.

DETAILED DESCRIPTION OF THE EMBODIMENTS

Amino acid sequences based on extraction and separation of a pyrethrin biosynthetic enzyme, a process leading to a procedure of base sequence determination of the gene thereof, vectors bearing the gene based on the thus determined base sequence, and transformants introducing such vectors of the present invention are explained as follows. However, the disclosed invention is not limited to the embodiments (1) to (4) discussed above or to the embodiments discussed in more detail below, but includes embodiments that can be easily substituted and considered from the embodiments described herein.

It is essential to ensure proteins composing a pyrethrin biosynthetic enzyme in advance of the embodiment according to steps in order of the following (a) to (d).

Figure 8:
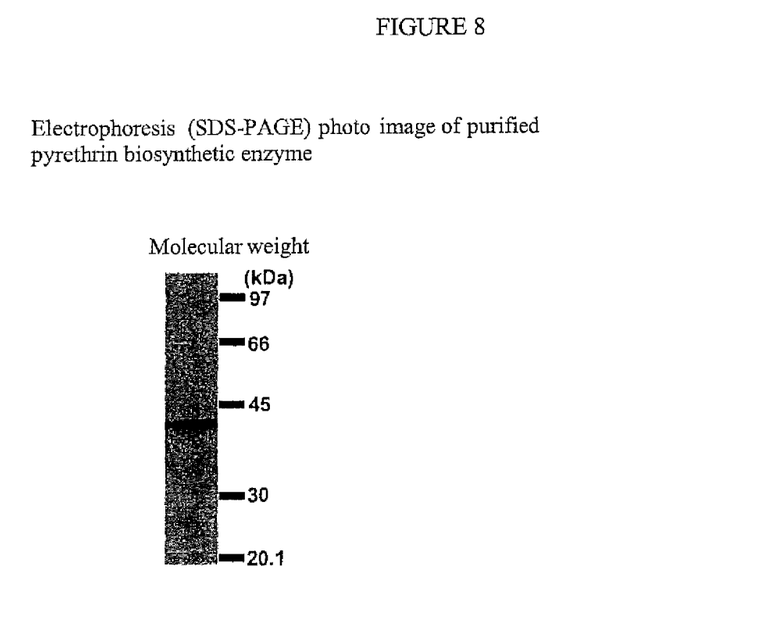
FIG. 8 is an electrophoresis (SDS-PAGE) photo image to clarify the degree of molecular weight identification to confirm the degree of purification of the pyrethrin biosynthetic enzyme produced in Example 1.

The inventors of the present invention performed fractionation and purification of a pyrethrin biosynthetic enzyme using a crude enzyme solution prepared from a pyrethrum flower as a raw material, (1R)-trans-chrysanthemoyl-CoA and (S)-pyrethrolone as substrates to confirm an active function of the pyrethrin biosynthetic enzyme, and pyrethrin I synthesis activity as an indicator. In other words, as is described in the above (1), fractionation, crude purification and purification were performed in order of crude fractionation by ammonium sulfate precipitation, crude purification by batch method using hydrophobic resin, purification with anion-exchange chromatography, hydrophobic chromatography and gel filtration column, and enzyme reactions to the above-described substrate were performed at each step. An enzyme was obtained by fractionating purified fractions concluded to have pyrethrin biosynthetic enzyme activity. A protein band of a molecular weight 40,000, which is expected to contribute to esterification reaction as an enzyme, was detected by SDS-PAGE of the enzyme (FIG. 8).

A produced pyrethrin biosynthetic enzyme protein was successfully secured by transferring the protein obtained by confirming the above band onto a PVDF membrane.

Meanwhile, a specific process through confirmation of the above band is described later in Example 1.

(A) Analysis of Crude Amino Acid Sequences of Enzyme Protein.

A purified enzyme secured as is described above was digested with trypsin, a protease, and fragmented into peptides. Then, digested peptide fragments were separated with HPLC, and amino acid residues of the separated peptides were singly disassembled and dissociated from the amino terminal end by the Edman method.

Amino acid residues were determined by analyzing produced phenylthiohydantoin derivatives with HPLC. This series of processes was performed using a peptide sequencer which is a special analytical instrument automated to repeat this reaction and analysis procedures.

As is described above, crude amino acid sequences constituting the pyrethrin biosynthetic enzyme protein were successfully obtained.

(B) Design of Primers and Determination for CDS.

Degenerate primers were designed based on base sequences estimated from determined amino acid sequences.

Unknown base sequences between known sequences were determined with PCR (Polymerase Chain Reaction) adopting the above primers (for example, four pairs of degenerate primers).

Next, a polynucleotide serving as an adaptor was previously added to DNA used as substrate of PCR. RACE-PCR was performed simultaneously using primers designed on an adaptor sequence and a known sequence, and DNA fragments containing sequences of both ends were amplified. The amplified DNA fragments were sequenced with DNA sequencer, and CDS was determined.

The CDS of the pyrethrin biosynthetic enzyme determined as is described above is shown in SEQ ID NO: 5 of FIG. 2.

Determination of a CDS No. 5 can also be achieved by other gene detection methods such as immunological screening methods for the above-described enzyme protein transferred onto a PVDF membrane, and hybridization method using nucleic acid probes as well as the above-described PCR.

(C) Determination for a Full Length of Amino Acid Sequence.

An amino acid sequence coded by the above-described gene corresponding to the above base sequence of SEQ ID NO: 5 was determined.

An amino acid sequence of a pyrethrin biosynthetic enzyme determined in the present invention is shown in SEQ ID NO: 1 of FIG. 1(a) and SEQ ID NO: 2 of FIG. 1(b).

Even though an amino acid sequence contains one or more of a substitution, deletion, insertion, and/or addition of an amino acid in the amino acid sequence of SEQ ID NO: 1, the protein is included in proteins of a pyrethrin biosynthetic enzyme of the present invention as long as the protein can be extracted from plants containing the pyrethrin biosynthetic enzyme using similar techniques and processes with an amino acid sequence of SEQ ID NO: 1, and the protein exhibits a function as a pyrethrin biosynthetic enzyme, because the protein is able to function in the same manner as the enzyme protein shown as SEQ ID NO: 1. Furthermore, amino acid sequences according to the following sequences also correspond to the protein as a pyrethrin biosynthetic enzyme of the present invention:

A sequence shown as SEQ ID NO: 2 in FIG. 1(b): An amino acid sequence where MBP (maltose binding protein) sequence was added to transform the initial part of the enzyme protein of SEQ ID NO:1 to express the protein as an MBP fusion protein in *E. coli*.

As is described later in Example 2, an amino acid sequence shown as SEQ ID NO: 1 is extracted from a pyrethrum flower, therefore it can be naturally purified, as is later described in Example 3, enzymes according to amino acid sequences shown as SEQ ID NO: 2 were obtained by introduction of a vector bearing a sequence encoding the amino acid sequence of SEQ ID NO: 1 into *E. coli* and expression of the protein in *E. coli*.

(D) Production of Vector and Transformants Introducing the Vector.

The vector of above (4) is produced by inserting any of the genes of above (3), and exhibits pyrethrin biosynthetic enzyme activity. The above vector can express the inserted gene or gene fragment in hosts such as plants and microorganisms by being introduced into the hosts by well-known transformation methods.

Also, a transformant having the vector of above (4) introduced therein refers to a transformant which introduces a gene or gene fragment related to pyrethrin biosynthesis into a host. The phrase "having the above vector introduced" used herein refers to that the gene inserted into the vector is introduced into a host in a manner capable of expressing such a gene using well-known genetic engineering techniques.

Methods for introducing genes include, but are not limited to, a transformation method with *Agrobacterium*, a particle gun method, a microinjection method and an electroporation method.

When the transformation method with *Agrobacterium* is used, the relevant gene is inserted into a Ti plasmid vector, the vector is introduced into *Agrobacterium*, and then the *Agrobacterium* is infected to the appropriate plant. A tumor (crown gall) is formed at the site of gene introduction. After elimination of *Agrobacterium*, many plant bodies regenerated from the crown gall are evaluated on activity, and plant bodies that highly express the pyrethrin biosynthetic enzyme can be selected.

Such transformants can express genes related to pyrethrin biosynthesis in their bodies. Therefore, a pyrethrin biosynthetic enzyme may be produced in large quantities by constructing transformants, which have the vector of above (4) bearing a promoter to express such an enzyme in large quantity by using bacterial chromosome and/or chloroplast of plants, blue-green algae, yeasts, or bacteria such as *E. coli* as a host.

Since the above-described vector contains a gene (or a gene fragment) of a pyrethrin biosynthetic enzyme derived from pyrethrum, plant chromosome and/or chloroplast are preferred as hosts for construction of transformants, in particular, chromosome and/or chloroplast of asteracea plants, which belong to the same family as pyrethrum, are more preferable. Such asteracea plants include, but are not limited to, marigold, African marigold, calendula and zinnia.

Above-described plants also include not only entire plant bodies but also a part of the plant bodies, for example, a leaf, seed, tuber, graft and the like. Furthermore, the above plants also include plant materials (a part of a plant including the flower, stem, fruit, leaf, and root) with growth potential, such as plant tissue, protoplast, cell, callus, organs, plant seed, germ, pollen, ovum, and zygote, derived from genetically-modified plants and progeny thereof transformed previously.

Pyrethrin can be produced by using either one of the protein of above (2) or the above transformants. The present invention provides such a pyrethrin production method. According to the method, pyrethrin can be produced effectively and easily using the above asteracea plants or other plants with obviously faster growth than pyrethrum, and thus, social demand seeking safe and environment-friendly insecticide could be greatly fulfilled by the present invention.

EXAMPLES

Hereinafter, details of the present invention will be concretely described by referring to Examples as follows.

Example 1

Figure 7:
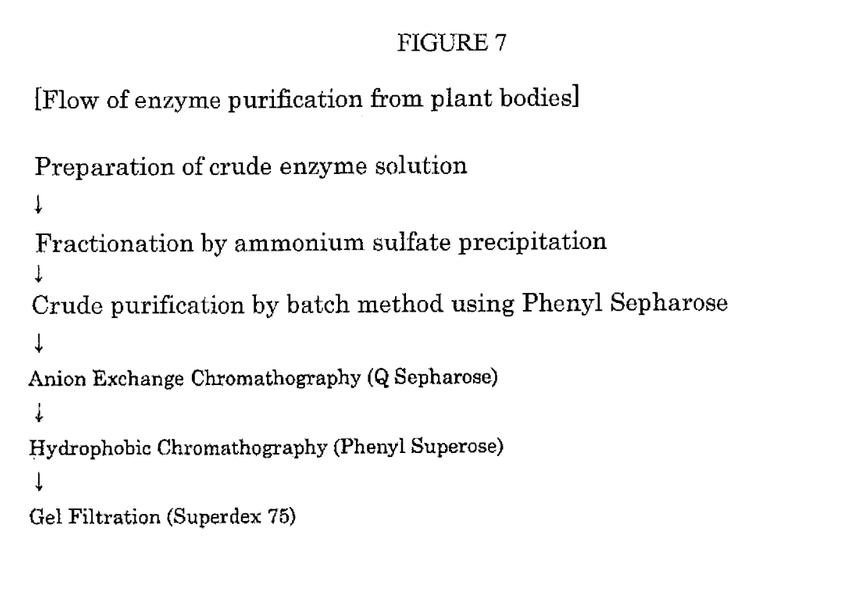
FIG. 7 is a flow diagram of the procedure for enzyme production from a pyrethrum flower in Example 1.

An enzyme was purified from pyrethrum flowers according to the procedures shown in FIG. 7 to analyze the above-described amino acid sequence of (a). Detailed explanations regarding the procedures are provided below.

Buffer Compositions Used for Purification

Compositions of buffers used for purification are shown in Tables 1 to 6.

TABLE 1

| Buffer A | |
|---|---|
| Constituent | Concentration (mM) |
| Tris-HCl, pH 8.0 | 50 |
| EDTA | 1 |
| DTT | 5 |
| Sodium Ascorbate | 100 |
| PMSF | 2 |

TABLE 2

| Buffer B | |
|---|---|
| Constituent | Concentration (mM) |
| Tris-HCl, pH 8.0 | 20 |
| EDTA | 1 |
| DTT | 5 |

TABLE 3

| Buffer C | |
|---|---|
| Constituent | Concentration (mM) |
| Tris-HCl, pH 8.0 | 20 |
| EDTA | 1 |
| DTT | 5 |
| NaCl | 500 |

TABLE 4

| Buffer D | |
|---|---|
| Constituent | Concentration (mM) |
| Tris-HCl, pH 8.0 | 20 |
| EDTA | 1 |
| DTT | 5 |
| NaCl | 150 |

TABLE 5

| Buffer E | |
|---|---|
| Constituent | Concentration (mM) |
| Tris-HCl, pH 8.0 | 20 |
| EDTA | 1 |
| DTT | 5 |
| $(NH_4)_2SO_4$ | 400 |

TABLE 6

| Buffer F | |
|---|---|
| Constituent | Concentration (mM) |
| Tris-HCl, pH 8.0 | 50 |
| EDTA | 1 |
| DTT | 5 |
| Sodium Ascorbate | 100 |
| $(NH_4)_2SO_4$ | 1000 |

Reaction of Pyrethrin Biosynthetic Enzyme

An enzyme reaction was assayed in each purification step, and enzyme activity of a pyrethrin biosynthetic enzyme in purified fractions was evaluated. A reaction was performed at 25° C. for 1 hour using the reaction composition shown in Table 7 as follows. After the enzyme reaction, 200 μl of hexane was added to the reaction solution. The organic phase was separated and collected therefrom, and 10 μl for each sample was used for HPLC analysis.

TABLE 7

| Composition for reaction of pyrethrin biosynthetic enzyme | | |
|---|---|---|
| | Volume (μl) | Concentration (mM) |
| Enzyme solution | 20 | |
| (1R)-trans-Chrysanthemoyl-CoA (10 mM aqueous solution) | 10 | 0.5 |
| (S)-Pyrethrolone (20 mM DMSO solution) | 4 | 1 |
| 250 mM Tris-HCl (pH 7.5), 1 mM EDTA | 40 | 50 |
| Water | 126 | |
| Total volume | 200 | |

Activity Measurement of Pyrethrin Biosynthesis Enzyme with HPLC

HPLC analysis was performed using SCL-10A VP (programming unit), DGU-14A (deaeration unit), LC-6AD (pump), CTO-10AS VP (sample injection and column oven unit), and SPD-10AV VP (optical detector) produced by SHIMADZU, and data were processed with CLASS-VP software from SHIMADZU. A Cadenza C-18 column from IMTAKT (0.46 cm I.D.×10 cm L.) was used, and absorption at 230 nm was measured at 40° C., at a flow rate of 1 ml/min. Acetonitrile:$H_2O$ (65:35) was used as mobile phase.

Figure 6:
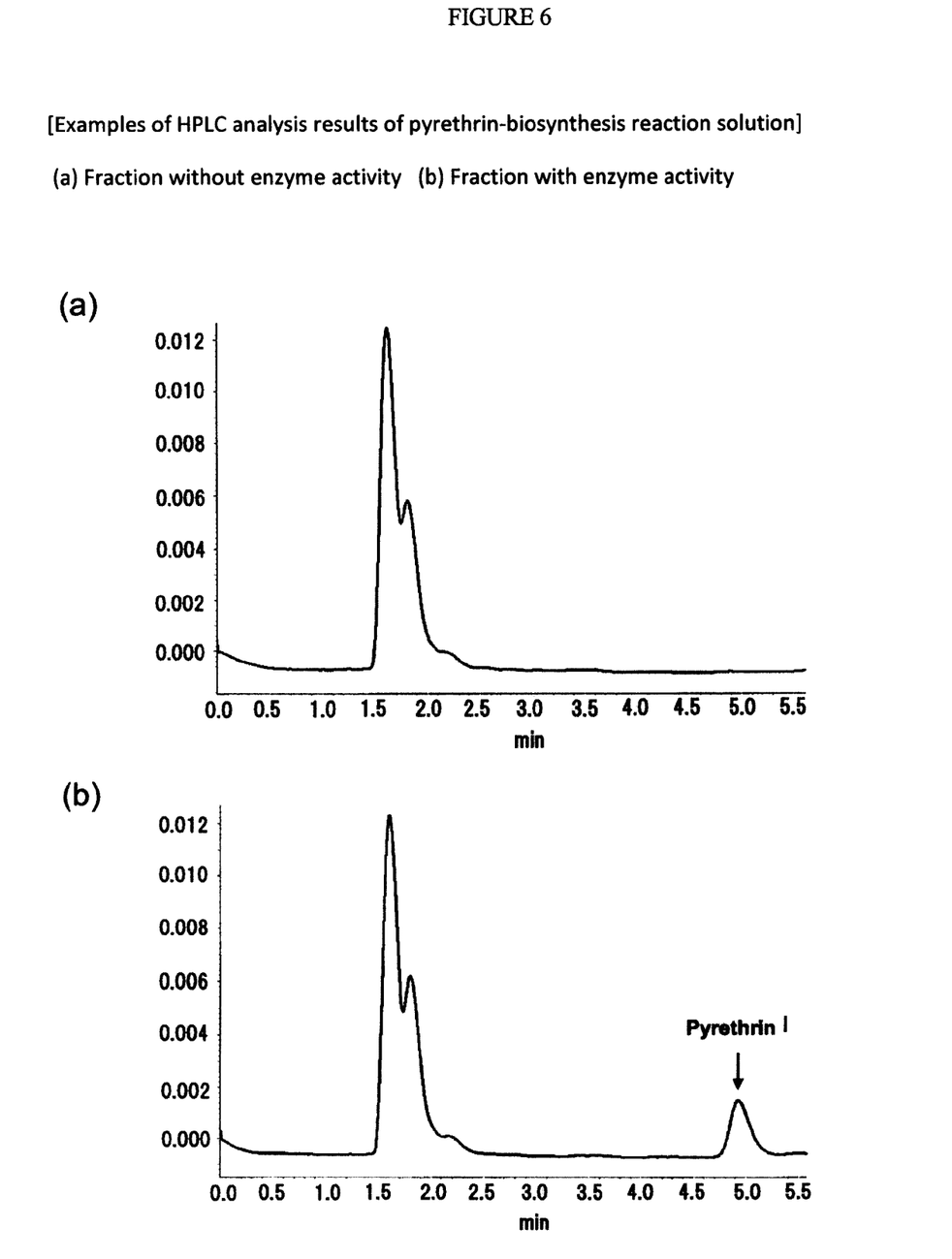
FIG. 6 shows graphs of measurement results of pyrethrin biosynthetic enzyme activity with HPLC of Example 1.

HPLC analysis results are exemplified in FIG. 6. Results of fractions without and with enzyme activity at the protein purification step are shown in FIGS. 6(a) and 6(b), respectively. As indicated in the figure, a peak of pyrethrin I was detected with 4.9 min of retention time in the course of elution time when the fractionated solution contains the enzyme.

Preparation of Crude Enzyme

A crude enzyme was prepared from 500 g of pyrethrum flower buds according to the following procedures. Ice cold 1.5 L of Buffer A and polyvinyl pyrrolidone (1/10 volume (w/v) of Buffer A) were added to the buds, and the buds were homogenized using a blender. A homogenate was filtered with a four-layered cheesecloth, and filtrate was centrifuged at 8,000×g for 20 min at 4° C. Collected supernatant was mixed with 100 mL of DOWEX (1×4, 100-200 Cl FORM) (Muromachi technos CO., LTD), stirred with a stirrer for 10 min, and centrifuged at 8,000×g for 20 min at 4° C. Supernatant was collected as a crude enzyme solution, and provided for further purification.

Fractionation by Ammonium Sulfate Precipitation

Ammonium sulfate was ground using a pestle and a mortar in advance, and resolved and mixed using a stirrer by portions into the crude enzyme solution obtained by the above-described preparation to a concentration of 30% saturation of ammonium sulfate. After allowing it to stand for 30 min, the solution was centrifuged at 8,000×g for 20 min at 4° C. (g represents gravitational acceleration). Supernatant was collected, and ammonium sulfate was added so that a concentration of ammonium sulfate becomes 80% saturation. After allowing it to stand for one night, the solution was centrifuged at 8,000×g for 20 min at 4° C. and the enzyme fraction was obtained as precipitate.

Crude Purification by Batch Method Using Hydrophobic Resin

The precipitate obtained by the above-described fractionation was suspended into Buffer F, and Phenyl Sepharose (GE Healthcare) was added to the solution. After mixing using a stirrer for 30 min, the mixture was separated using a Buchner funnel. Phenyl Sepharose remaining in the Buchner funnel was washed with 500 mL of Buffer F, and then protein absorbed by the resin was eluted with 500 mL of Buffer B. Ammonium sulfate was added into the collected elute to 1 M of concentration, and then 20 mL of Phenyl Sepharose (GE Healthcare) was added to the solution. After mixing using a stirrer for 30 min, the mixture was transferred and settled in Econo-Column (Bio-Rad), protein absorbed by the resin was eluted with 50 mL of Buffer B. Eluate was transferred into a cellophane dialysis tubing, dialyzed in 2 L of desalting buffer for 2 hours by stirring the buffer using a stirrer, and followed by another desalting after buffer change for 3 hours. The desalted enzyme solution was further purified by column chromatography using an AKTA explorer (GE Healthcare) system.

Purification with Anion-Exchange Chromatography

The enzyme solution obtained by the above-described crude purification with the batch method was further purified by anion-exchange chromatography using a Q Sepharose column according to the following conditions.

TABLE 8

| System | ÄKTA explorer 10s |
|---|---|
| Column | HiPrep ™ 16/10 Q FF (GE Healthcare) |
| Pump A | Buffer B |
| Pump B | Buffer C |
| Equilibration | (A) 100% |
| Sample | Desalted enzyme solution after batch treatment with Phenyl Sepharose |
| Rinse | (A) 100%, 100 mL |
| Elution | (B) 0-100% in 400 mL |
| Flow rate | 4 mL/min |
| Fraction | 10 mL/tube |

Purification with Hydrophobic Chromatography

The enzyme solution obtained by the above-described anion-exchange chromatography was further purified by hydrophobic chromatography using a Phenyl Superose column according to the following conditions.

TABLE 9

| System | ÄKTA explorer 10s |
|---|---|
| Column | Phenyl Superose FPLC ® (GE Healthcare) |
| Pump A | Buffer E |
| Pump B | Buffer B |
| Equilibration | (A) 100%, 10 mL |
| Sample | Enzyme solution purified with anion-exchange chromatography |
| Rinse | (A) 100% |
| Elution | (B) 0-100% in 20 mL |
| Flow rate | 0.4 mL/min |
| Fraction | 2 mL/tube |

Purification with Gel Filtration

The enzyme solution obtained by the above-described hydrophobic chromatography was further purified by gel filtration using a Superdex 75 column according to the following conditions.

TABLE 10

| System | ÄKTA explorer 10s |
|---|---|
| Column | Superdex 75 HR 10/30 (GE Healthcare) |
| Buffer | Buffer D |
| Sample | Active fractions purified with Phenyl Sepharose |
| Flow rate | 0.5 mL/min |
| Fraction | 0.5 mL/tube |

An enzyme purified by the above-described methods was separated with SDS-PAGE, and the degree of purification was confirmed with silver staining. The result of silver staining is shown in FIG. 8. A single protein band of the pyrethrin biosynthetic enzyme with a molecular weight of approximately 40,000 was detected.

Example 2

Procedures from analysis of the above-described crude amino acid sequence (a) or (b) to determination of a full length amino acid sequence of the pyrethrin biosynthetic enzyme obtained in Example 1, further, preparation of transformant introducing a vector bearing a gene, which codes protein of the above-described amino acid sequence, were performed as follows.

Analysis of Amino Acid Segments Including Pyrethrin Biosynthetic Enzyme Protein

The protein band obtained in Example 1 was excised from a gel, and used as a sample for analysis of an internal amino acid sequence. Also, the band of an SDS-PAGE was transferred to a PVDF membrane, detected with Coomassie Blue staining, and the excised band was used for N-terminal amino acid analysis. This series of manipulations was performed according to well-known methods.

Figure 9:
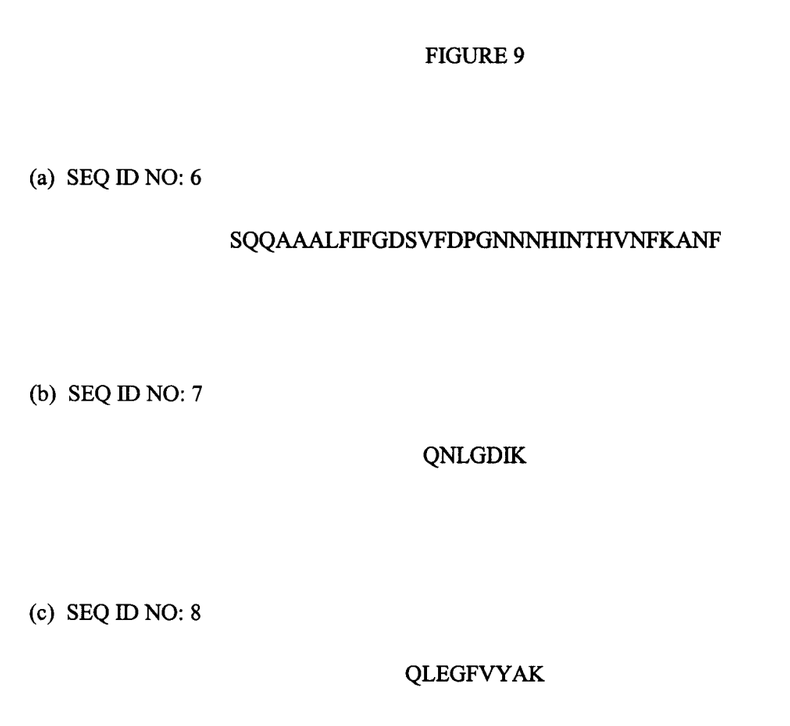
FIG. 9 lists crude amino acid sequences obtained by analyzing each part of amino acids constructing a pyrethrin biosynthetic enzyme protein.

As a result of the above-described amino acid analyses, examples of crude amino acid sequences, SEQ ID NOS: 6,7 and 8, including the enzyme protein shown in FIGS. 9(*a*), 9(*b*) and 9(*c*) were confirmed, respectively.

Design of Primers and Determination of a CDS

A CDS (FIG. 2, SEQ ID NO: 5) and amino acid sequence (FIG. 1(*a*), SEQ ID NO: 1) were determined according to the above-described methods based on amino acid sequences determined by amino acid analyses. Methods used in this series of manipulations, including cDNA preparation, PCR, and sequence analysis using DNA sequencer, were performed according to well-known methods.

Determination for a Full-Length of Amino Acid Sequence

The N-terminal amino acid sequence of the pyrethrin biosynthetic enzyme determined by the above analysis is a sequence without a portion from the N-terminal to serine (S) 27 of the amino acid sequence of SEQ ID NO: 1, as shown in FIG. 1(*b*), SEQ ID NO: 2. And, as is described above, while the truncated amino acid sequence shown in SEQ ID NO: 2 corresponds to the sequence for the protein, which has enzyme activity in pyrethrum, the removed 27 amino acid residues are a signal sequence for translocation, which has a function to ensure conditions for smooth pyrethrin biosynthesis. Therefore, the sequence of FIG. 1(*a*) including the above 27 amino acid residues, i.e., amino acid sequence of SEQ ID NO: 1, corresponds to the sequence of the pyrethrin biosynthetic enzyme including such a signal sequence for translocation.

Meanwhile, a protein with amino acid sequences of SEQ ID NOS: 3 and 4 is obtained by abundant expression of a gene encoding a protein with amino acid sequence of SEQ ID NO: 1, which are integrated into a vector and introduced into *E. coli*. It has already been pointed out in embodiment (c) of the present invention that this protein has a high possibility of having activity of a pyrethrin biosynthetic enzyme and to exist in plants, which is capable of producing pyrethrin.

Production of Vector and Transformant

Construction of vector and transformant bearing the above-described pyrethrin biosynthetic enzyme gene were performed as follows.

Available vector in the present invention includes existing vectors used for transformation of microorganisms, plants, and plant cells. It is substantially predictable based on common knowledge of one skilled in the art that such vectors are able to contain a constitutive or inducible promoter to express known genes; a protein of facilitating solubilization and purification of expressed protein such as a histidine-tag, glutathione S-transferase; fusion protein such as maltose-binding protein; a drug resistance gene facilitating selection of transformants, and replication origins for binary vector system of *Agrobacterium* in addition to a part of the above full length gene encoding the above pyrethrin biosynthetic enzyme.

Specifically, for example, pET vector (Novagen), pGEX vector (GE Healthcare), and pMAL vector (New England Biolab) can be used for introduction to microorganisms such as *E. coli*. Vectors appropriate for introduction into plants with *Agrobacterium* include pBI101 and pBI121. There is no specific limitation on the type of vectors when the vector is introduced into plant cells by electroporation or particle gun method. Also, the above drug resistance genes include resistance genes of ampicillin, kanamycin and hygromycin. As examples of the above promoters, 35S promoter derived from a cauliflower mosaic virus (constitutive promoter) or promoters of heat shock-induced proteins (inducible promoter) can be used. Replication origins include replication origins derived from Ti or Ri plasmids. It is substantially predictable that construction of these transformants is feasible based on common knowledge of one skilled in the art.

When the above-described transformants are constructed with microorganisms such as *E. coli* and yeast, conversion of a substance using a microbial cell system becomes possible. Furthermore, construction of the above-described transformants using asteracea plants such as African marigold, calendula and zinnia, which are known to produce a small amount of pyrethrin for less than practical use, and improvement in ability of pyrethrin synthesis enable effective production of pyrethrin in plants which grow faster than pyrethrum. Thus, this is useful for production of insecticides.

Example 3

Protein Expression and Purification

All the TcGLIP variants were expressed as fusions of the maltose binding protein (MBP) as follows. The cDNA was amplified by PCR using KOD-Plus DNA polymerase (Toyobo, Osaka, Japan) with primers (SEQ ID NO: 9—5'-CCGGAATTCCTGGAAGTTCTGTTC-CAGGGGCCCTCTCAACAAGCTGCTGCACT-3' and SEQ ID NO: 10—5'-CCCAAGCTTTAGAGCTCAT-CATTTGGGAG-3'), 0.2 mM dNTP, 1 mM MgSO4 and template cDNA. The PCR was conducted with 30 cycles of 94° C. 15 sec, 56° C. 30 sec and 68° C. 2 min. following the first denaturing step of 94° C. 2 min. The PCR product was cloned in the EcoR I and Hind III sites of the pMAL-c4E vector (NEW England Biolabs Japan, Tokyo, Japan). The *E. coli* BL21 (DE3) pLysS strain was transformed with the plasmid construct and then cultured with shaking. The enzyme was over-expressed in the bacterial strain by inducing with 0.5 mM isopropyl-β-D-thiogalactopyranoside. The bacteria were harvested by centrifugation and sonicated for disruption. Resultant protein mixture was purified by affinity chromatography with the Amylose resin (New England Biolabs) followed by anion exchange chromatography with a Mono Q column (GE Healthcare Japan, Tokyo, Japan) to obtain the MBP fusion of the enzyme with the sequence shown in SEQ ID NO:2.

Acyltransferase Activity

The acyltransferase activity was measured in a 100 μL solution consisting of 100 mM Tris (pH 7.5), 0.5 mM CoA ester, 1 mM (1S)-pyrethrolone and 500 ng purified enzyme at 25° C. for 10 min. The reaction was stopped with 10 μL acetic acid and extracted with 100 μL hexane. The extract was subjected to HPLC of pyrethrin I and II in terms of absorbance at 230 nm. The HPLC was carried out using a Cadenza CD-C18 column (Imtakt, Kyoto, Japan) with a solvent system of $CH_3CN/H_2O$ at 1 ml/min at 40° C., when $CH_3CN$ was mixed with $H_2O$ at 80:20 and 65:35 to detect pyrethrin I and II, respectively. Pyrethrins were quantified by comparing their external standards.

The recombinant enzymes were expressed as MBP fusions by *E. coli*. Except for the SP sequence, variations in the amino acid sequence of the TcGLIP were seen at positions of 103, 227, 249, 253 and 359 (Table 11). We newly determined the specific acyltransferase activities of the recombinant enzyme expressed by a cDNA of accession number JN418994 to be 1.09 and 0.45 nkat/mg protein for pyrethrin I and II synthesis, respectively (Table 12). Whatever the variations, all the variants displayed a higher acyltransferase activity for pyrethrin I than pyrethrin II. The acyltransferase activities of variants JN418993 and JN418996 were similar. Hence the amino acid at positions of 103 and 359 had no critical role for the activity. However, JN418994 showed a slightly higher activity than JN418993 and JN418996, suggesting that Asp103 and Tyr359, when combined, may contribute to enhancing the activity. A greater, reproducible difference of the activity was observed between JN418990 and the other variants regardless of whether the acyl CoA substrate is chrysanthemoyl CoA or pyrethroyl CoA (Table 12). Conceivably, at least one of Ala227, His249 and Glu253 underlies such a difference. Further experiments are needed to clarify which residue most influences the pyrethrin synthesis activity, yet this result helps design TcGLIPs with high performance.

TABLE 11

Comparison of the amino acid sequence of TcGLIP variants

| Accession number | Amino acid numbers[1] (from Met1) | | | | |
|---|---|---|---|---|---|
| | 103 | 227 | 249 | 253 | 359 |
| JN418990 | Asp | Ala | His | Glu | Phe |
| JN418993 | Asp | Thr | Gln | Gln | Phe |
| JN418994 | Asp | Thr | Gln | Gln | Tyr |
| JN418996 | Tyr | Thr | Gln | Gln | Tyr |

[1]Only amino acids differing among the variants are shown except for the signal peptide sequence.

TABLE 12

Acyltransferase activities of TcGLIP variants for pyrethrin synthesis

| Accession numbers | Specific activity (nkat/mg protein)[1] | | Relative specific activity(Percent) | |
|---|---|---|---|---|
| | Pyrethrin I | Pyrethrin II | Pyrethrin I | Pyrethrin II |
| JN418990 | 1.40 ± 0.01[2] | 0.578 ± 0.019[2] | 128 | 53.0 |
| | 1.42 ± 0.02[2] | 0.581 ± 0.016[2] | 130 | 53.3 |
| JN418993 | 1.02 ± 0.02 | 0.411 ± 0.011 | 93.6 | 37.7 |
| JN418994 | 1.09 ± 0.01[3] | 0.451 ± 0.004[3] | 100 | 41.4 |
| JN418996 | 0.992 ± 0.019 | 0.399 ± 0.013 | 91.0 | 36.6 |

[1]Specific activity values are shown as mean ± standard error of the mean of triplicated experiments.
[2]Two separate protein expressions were carried out to determine the acyltransferase activity of JN418990. The upper data was determined at the same time with the data of JN418993 and JN418996, whereas the lower data was determined at the same time with that of JN418994.
[3]The data for the variant JN418994 were newly determined for this report.

The present invention discloses amino acid sequences of enzymes related to pyrethrin biosynthesis and a base sequence of a gene thereof, and thus provides perspective that highly useful and safe pyrethrin as a raw material of insecticides can be inexpensively and effectively produced by using fast growing plants. Therefore, this indicates a possibility that the present invention can make a great contribution to the insecticide industry.

Furthermore, the present invention can be used in all industrial areas using pyrethroids for insecticides, in particular, the area of insecticidal instruments and devices using pyrethroids as active ingredients, such as mosquito/fly coils, insecticide sprays, heat and transpiration devices for liquid insecticides, and electrothermal mosquito mats.

What is claimed is:

1. A protein consisting of the amino acid sequence set forth in SEQ ID NO: 2.

2. An isolated polynucleotide encoding a protein consisting of the amino acid sequence set forth in SEQ ID NO: 2.

3. A vector comprising the isolated polynucleotide according to claim 2.

4. A recombinant cell comprising the vector of claim 3.

* * * * *